United States Patent
Cho et al.

(10) Patent No.: US 10,839,546 B2
(45) Date of Patent: Nov. 17, 2020

(54) METHOD AND APPARATUS FOR CONTINUOUSLY DETECTING HAZARDOUS AND NOXIOUS SUBSTANCE FROM MULTIPLE SATELLITES

(71) Applicant: Korea Institute of Ocean Science & Technology, Daejeon (KR)

(72) Inventors: Deuk Jae Cho, Daejeon (KR); Moon Jin Lee, Daejeon (KR)

(73) Assignee: Korea Institute of Ocean Science & Technology, Gyeonggi-do (KR)

( * ) Notice: Subject to any disclaimer, the term of this patent is extended or adjusted under 35 U.S.C. 154(b) by 287 days.

(21) Appl. No.: 15/781,563

(22) PCT Filed: Oct. 24, 2016

(86) PCT No.: PCT/KR2016/011975
§ 371 (c)(1),
(2) Date: Jun. 5, 2018

(87) PCT Pub. No.: WO2017/099346
PCT Pub. Date: Jun. 15, 2017

(65) Prior Publication Data
US 2020/0294263 A1 Sep. 17, 2020

(30) Foreign Application Priority Data
Dec. 8, 2015 (KR) .................. 10-2015-0173899

(51) Int. Cl.
*G06T 7/70* (2017.01)
*G01S 13/72* (2006.01)
*G06T 7/60* (2017.01)

(52) U.S. Cl.
CPC .............. *G06T 7/70* (2017.01); *G01S 13/726* (2013.01); *G06T 7/60* (2013.01)

(58) Field of Classification Search
CPC . B60W 2050/0078; B60W 2554/4041; B60W 2554/801; B60W 2556/50;
(Continued)

(56) References Cited

U.S. PATENT DOCUMENTS 7,925,167 B1 * 4/2011 Kozubal ............... H04B 10/118
398/125
8,396,286 B1 * 3/2013 Aradhye ............ G06K 9/00718
382/159

(Continued)

FOREIGN PATENT DOCUMENTS

EP 2610636 A1 7/2013
KR 20020054215 A 7/2002
(Continued)

OTHER PUBLICATIONS

International Search Report PCT/ISA/210 for International Application No. PCT/KR2016/011975 dated Jan. 25, 2017.
(Continued)

*Primary Examiner* — Aklilu K Woldemariam
(74) *Attorney, Agent, or Firm* — Harness, Dickey & Pierce, P.L.C.

(57) ABSTRACT

The present invention relates to a method and an apparatus for continuously detecting a hazardous and noxious substance from multiple satellites, and specifically, provides a method and an apparatus for continuously detecting a hazardous and noxious substance from multiple satellites, the method and apparatus: receiving a multi-satellite image which is photographed by a multi-satellite comprising a satellite having an imaging radar (SAR), a satellite having an infrared sensor, and a satellite having an electronic optical
(Continued)

| Sensor | Agency | Wavelength (cm) | Polarization | Resolution (m) | Period of Operation | Incidence Angle (°) | Swath (km) |
|---|---|---|---|---|---|---|---|
| TerraSAR-X | DLR | 3.1 (X-Band) | HH,VV, HV,VH | 0.25-40 | Jun 2007-Present | 15-60 | 10-100 |
| Cosmo_SkyMED1 | ASI | 3.1 (X-Band) | HH,VV, HV,VH | 1-100 | Jul 2007-Present | 20-59 | 10-200 |
| RADARSAT-2 | CSA | 5.7 (C-Band) | HH,VV, HV,VH | 3-100 | Dec 2007-Present | 10-60 | 20-500 |
| Cosmo-SkyMED2 | ASI | 3.1 (X-Band) | HH,VV, HV,VH | 1-100 | Dec 2007-Present | 20-59 | 10-200 |
| Cosmo-SkyMED3 | ASI | 3.1 (X-Band) | HH,VV, HV,VH | 1-100 | Oct 2008-Present | 20-59 | 10-200 |
| TanDem-X | DLR | 3.1 (X-Band) | HH,VV, HV,VH | 12 | Jun 2010-Present | 20-55 | 30 |
| Cosmo_SkyMED4 | ASI | 3.1 (X-Band) | HH,VV, HV,VH | 1-100 | Nov 2010-Present | 20-59 | 10-200 |
| KOMSAT-5 | KARI | 3.2 (X-Band) | HH,VV, HV,VH | 1-20 | Aug 2013-Present | 20-55 | 5-100 |
| Sentinel-1 | ESA | 18 (C-Band) | single/Dual pol | 9-50 | Apr 2014-Present | 20-45 | 80-400 |
| ALOS-2 | JAXA | 22.9 (L-Band) | Single/Dual pol | 1-100 | May 2014-Present | 8-70 | 25-350 | sensor; acquiring a reference image, of the satellite having the SAR, including a ground control point of an observed region; extracting a corresponding point between the reference image and the multi-satellite image; implementing the image matching and geometric correction for the multi-satellite image by using the extracted corresponding point; confirming at least one among the brightness value of pixels of the SAR satellite image, the temperature value of pixels of the infrared satellite image or the color value of pixels of the optical satellite image which are included in the corrected multi-satellite image so as to detect the hazardous and noxious substance, and determine the flow information, thereby detecting continuously and stably the hazardous and noxious substance.

8 Claims, 6 Drawing Sheets

(58) Field of Classification Search
CPC ... B60W 2754/10; B60W 30/16; G01S 19/49; G01S 19/53; H04N 7/185; H04N 13/117; H04N 13/221; H04N 13/243; H04N 13/383; H04N 5/23238; H04N 7/181; H04N 7/183; H04N 5/23219; H04N 5/3454; G01C 21/3623; G01C 11/025; G01C 21/3647; G02B 30/00; G06T 3/0037; G06T 7/97; G06T 7/73; G06T 7/74; G06T 2207/10032; G06T 7/33; G01J 2003/2826; G01J 3/513; G01J 3/0289; G01J 3/18; G06K 2009/4666; G06K 9/00228; G06K 9/6267; G06K 9/3233; G06K 9/4671; G06K 9/00664; G06K 9/00221; G06K 9/00624; G06K 9/66; G06K 9/6202; G06K 9/6255; G06K 9/00281; G06K 9/52; G06F 3/0304
USPC .... 382/103, 199, 282; 348/47, 48, 143, 144, 348/164
See application file for complete search history.

(56) References Cited

U.S. PATENT DOCUMENTS

| | | | |
|---|---|---|---|
| 10,546,195 B2* | 1/2020 | Lo | G06K 9/00657 |
| 2006/0238617 A1* | 10/2006 | Tannin | H04N 5/2723 |
| | | | 348/143 |
| 2011/0106428 A1* | 5/2011 | Park | G01C 21/3623 |
| | | | 701/533 |
| 2012/0011142 A1* | 1/2012 | Baheti | G06K 9/4671 |
| | | | 707/769 |
| 2012/0033852 A1* | 2/2012 | Kennedy | G06K 9/00 |
| | | | 382/103 |
| 2012/0147149 A1* | 6/2012 | Liu | G06T 7/75 |
| | | | 348/50 |
| 2013/0033598 A1* | 2/2013 | Milnes | H04N 7/185 |
| | | | 348/144 |
| 2013/0335566 A1* | 12/2013 | Coulter | H04N 7/181 |
| | | | 348/144 |
| 2014/0064554 A1* | 3/2014 | Coulter | G06T 7/33 |
| | | | 382/103 |
| 2014/0201126 A1* | 7/2014 | Zadeh | A61B 5/165 |
| | | | 706/52 |
| 2014/0355887 A1* | 12/2014 | Kurosawa | G06T 7/12 |
| | | | 382/199 |
| 2016/0092735 A1* | 3/2016 | Govil | G06K 9/3233 |
| | | | 382/103 |
| 2016/0094814 A1* | 3/2016 | Gousev | G06K 9/00973 |
| | | | 348/143 |

FOREIGN PATENT DOCUMENTS

| | | |
|---|---|---|
| KR | 20100011549 A | 2/2010 |
| KR | 20150049836 A | 5/2015 |
| KR | 101534618 B1 | 7/2015 |

OTHER PUBLICATIONS

Written Opinion of the International Searching Authority PCT/ISA/237 for International Application No. PCT/KR2016/011975 dated Jan. 25, 2017.

* cited by examiner

【Figure 1】

| Sensor | Agency | Wavelength (cm) | Polarization | Resolution (m) | Period of Operation | Incidence Angle (°) | Swath (km) |
|---|---|---|---|---|---|---|---|
| TerraSAR-X | DLR | 3.1 (X-Band) | HH,VV, HV,VH | 0.25-40 | Jun 2007-Present | 15-60 | 10-100 |
| Cosmo_SkyMED1 | ASI | 3.1 (X-Band) | HH,VV, HV,VH | 1-100 | Jul 2007-Present | 20-59 | 10-200 |
| RADARSAT-2 | CSA | 5.7 (C-Band) | HH,VV, HV,VH | 3-100 | Dec 2007-Present | 10-60 | 20-500 |
| Cosmo-SkyMED2 | ASI | 3.1 (X-Band) | HH,VV, HV,VH | 1-100 | Dec 2007-Present | 20-59 | 10-200 |
| Cosmo-SkyMED3 | ASI | 3.1 (X-Band) | HH,VV, HV,VH | 1-100 | Oct 2008-Present | 20-59 | 10-200 |
| TanDem-X | DLR | 3.1 (X-Band) | HH,VV, HV,VH | 12 | Jun 2010-Present | 20-55 | 30 |
| Cosmo_SkyMED4 | ASI | 3.1 (X-Band) | HH,VV, HV,VH | 1-100 | Nov 2010-Present | 20-59 | 10-200 |
| KOMSAT-5 | KARI | 3.2 (X-Band) | HH,VV, HV,VH | 1-20 | Aug 2013-Present | 20-55 | 5-100 |
| Sentinel-1 | ESA | 18 (C-Band) | single/Dual pol | 9-50 | Apr 2014-Present | 20-45 | 80-400 |
| ALOS-2 | JAXA | 22.9 (L-Band) | Single/Dual pol | 1-100 | May 2014-Present | 8-70 | 25-350 |

[Figure 2]

| Sensor | | Agency | Period | Channel | Spectral coverage (nm) | Resolution (m) | Swath (km) |
|---|---|---|---|---|---|---|---|
| Landsat-7 ETM+ | | NASA /USGS | Apr 1999 - Present | Visible (3) NIR (1) SWIR (2) TIR (1) Panchromatic (1) | 441 - 12,360 | 30 - 60 | 185 |
| MODIS - Terra | | NASA | May 1999 - Present | Visible (11) NIR (7) SWIR (2) TIR (16) | 405 - 14,385 | 250 - 1000 | 2,330 |
| MODIS - Aqua | | | Dec 2002 - Present | | | | |
| ASTER | | NASA | Dec 1999 - Present | Visible (2) NIR (1) SWIR(6) TIR (5) | 520 - 11,650 | 15 - 90 | 60 |
| AVHRR3 | NOAA-16 | NOAA | Sep 2000 - Jun 2014 | Visible (1) NIR (1) MIR (1) TIR (2) | 580 - 12,500 | 1100 | 2,399 |
| | NOAA-17 | | Jun 2002 - Apr 2014 | | | | |
| | NOAA-18 | | May 2005 - Present | | | | |
| KOMPSAT-2 | | KARI | Jul 2006 Present | Visible (3) NIR (1) Panchromatic (1) | 450-900 | 1-4 | 15 |
| GOCI | | KIOST | Jun 2010 - Present | Visible (6) NIR (2) | 400-865 | 500 | 2,500 |
| KOMPSAT-3 | | KARI | May 2012 -Present | Visible (3) NIR (1) Panchromatic (1) | 450-900 | 0.7-2.8 | 15 |
| Landsat-8 OLI | | NASA /USGS | Feb 2013 - Present | Visible (4) NIR (1) SWIR (2) TIR (2) Panchromatic (1) Cirrus clouds (1) | 430 - 12,510 | 15-30 | 185 |

METHOD AND APPARATUS FOR CONTINUOUSLY DETECTING HAZARDOUS AND NOXIOUS SUBSTANCE FROM MULTIPLE SATELLITES

CROSS-REFERENCE TO RELATED APPLICATIONS

This application is a national phase under 35 U.S.C. § 371 of PCT International Application No. PCT/KR2016/011975 which has an International filing date of Oct. 24, 2016, which claims priority to Korean Application No. 10-2015-0173899, filed Dec. 8, 2015, the entire contents of each of which are hereby incorporated by reference.

TECHNICAL FIELD

The present invention relates to continuous detection method and apparatus of HNS from multiple satellites. More particularly, the present invention relates to continuous detection method and apparatus of HNS from multiple satellites, the method and apparatus being capable of continuously and accurately detecting HNS leaked into the ocean by using a SAR satellite image obtained from a satellite including a SAR, an infrared satellite image obtained from a satellite including an infrared sensor, and an optical satellite image obtained from a satellite including an electro optical sensor.

BACKGROUND ART

Recently, international transportation of hazardous and noxious substances (HNS) which is dependent on marine transportation, has grown rapidly. In addition, with the development of a large-scale economy and technology, the marine transportation environment, for example, the size and speed of vessels, is changing. This means that HNS such as crude oil, petroleum refined products, chemical substances etc. are transported in large quantities, thus maximizing efficiency, but as the total transport volume increases, the inherent risk also increases.

As described above, interest in HNS safety management is increasing based on the increase in HNS handling volume and recognition of the risk of domestic and international pollution accidents. Therefore, as the risk of marine HNS accident increases, efforts are currently being undertaken to construct a global HNS monitoring system.

Figure 1:
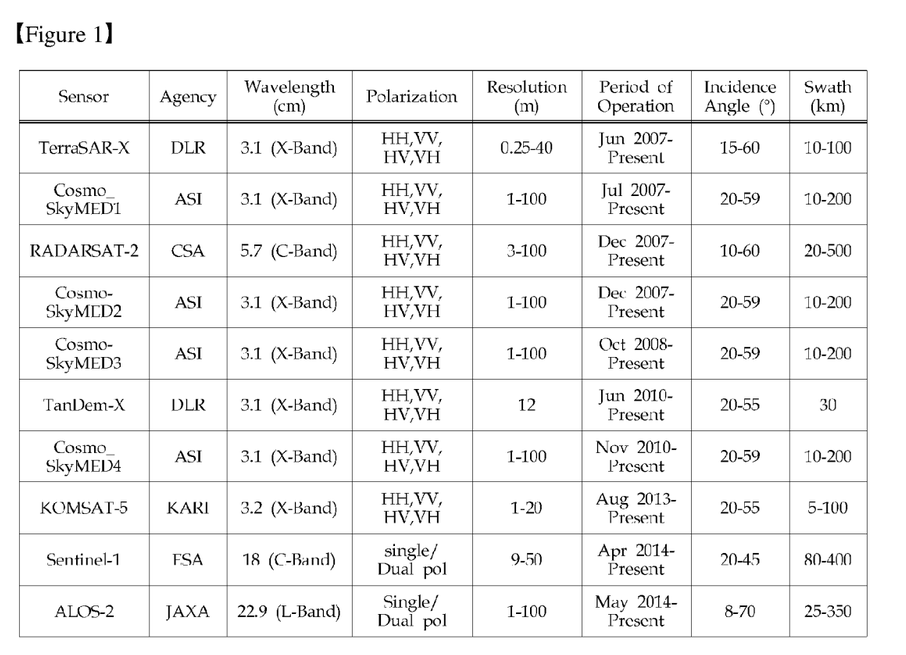
FIG. 1 is a view showing basic specifications of a main satellite including a SAR including currently in operation.

Meanwhile, an artificial satellite SAR (synthetic aperture radar) is a high resolution imaging radar that is not affected by weather conditions such as clouds and rain, and is one of typical active type sensors that images the surface of the earth by radiating microwaves toward the earth and using energy information that is returned by being scattered. FIG. 1 is a view showing basic specifications of a main satellite including a SAR currently in operation. The major advantage of a SAR sensor is that observation is performed for a wide spatial area from several tens km up to 500 km with a high resolution of several meters or less, and may be actively used for marine environmental monitoring. Particularly, the SAR sensor may perform monitoring under all weather conditions and is not affected by bad weather conditions and bad climate conditions such as clouds and fog, and can be used at day and night.

However, due to the characteristic of the active type sensor such as SAR sensor, the temporal resolution is lowered as an observation frequency is low.

Figure 2:
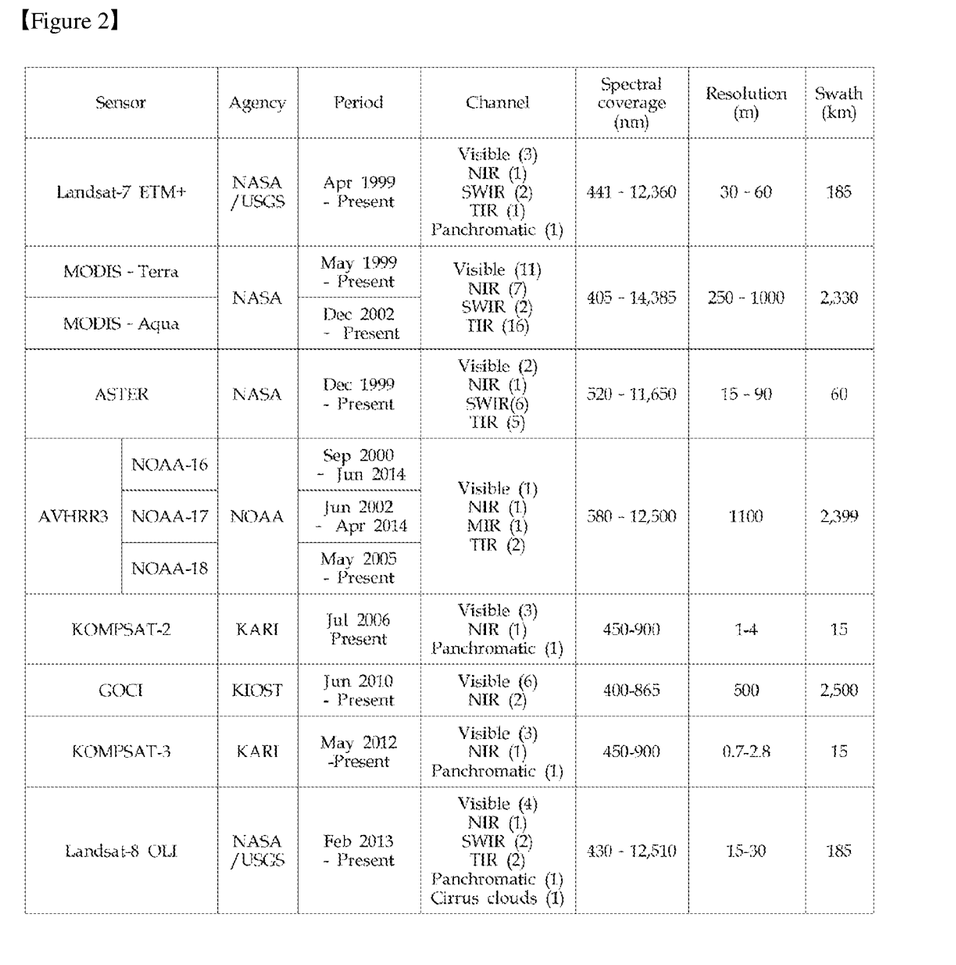
FIG. 2 is a view showing basic specifications of main satellites including optical and infrared sensors currently in operation.

FIG. 2 is a view showing basic specifications of a main satellite including optical and infrared sensors currently in operation since 2000. An optical sensor provides excellent resolution, but is mainly used at day time since the sensor uses the optical spectrum of reflected sunlight. Meanwhile, an infrared sensor provides poor resolution, but is used at day and night times, under foggy and cloudy conditions since the sensor uses heat radiated from an object. In addition, the infrared sensor also provides thermal resolution imaging.

In case of Landsat-7/8, advanced space borne thermal emission and reflection radiometer (ASTER) which are most widely used to obtain earth observation satellite data, high-resolution data of 30 m or less on visible channels is provided. In case of multipurpose utility satellite No. 2 and No. 3 (KOMPSAT-2/3) operated in Korea, high resolution images of one meter or less which are higher than the former case are provided.

In addition, geostationary ocean color imager (GOCI), the world's first geostationary orbital ocean observing satellite, observes sea areas around the Korean peninsula eight times a day, and thus enabling quasi-real-time monitoring. An advanced very high resolution radiometer (AVHRR)-3 which is an infrared sensor is a sensor included in National Oceanic and Atmospheric Administration (NOAA) series, observes the sea level at a resolution of about 1 km, and is mainly used for calculating the temperature of the sea level. Observation data obtained from infrared sensors such as AVHRR, etc. provide lower resolution than observation data obtained by using other visible lights, but wide areal observations in the range of several thousands of km may be performed.

When HNS have leaked into the ocean, the ocean becomes polluted by HNS, and thus the risk of accidents such as destruction of marine ecosystems increases and affected area are expanded. Therefore, rapid action is required to minimize damage, and thus stable and continuous monitoring of leakage of HNS in the ocean is also required.

DISCLOSURE

Technical Problem

Accordingly, the present invention has been made keeping in mind the above problems occurring in the prior art, and an object of the present invention is to provide continuous detection method and apparatus of HNS from multiple satellites, the method and apparatus being capable of continuously and accurately detecting HNS leaked into the ocean by using a SAR satellite image obtained from a satellite including a SAR, an infrared satellite image obtained from a satellite including an infrared sensor, and an optical satellite image obtained from a satellite including an electro optical sensor.

Technical Solution

In order to accomplish the above object, the present invention provides a continuous detection apparatus of HNS from multiple satellites, the apparatus including: a multi-satellite image obtaining unit receiving a multi-satellite image captured by a multi-satellite including a satellite including a SAR, a satellite including an infrared sensor, and a satellite including an electro optical sensor; a SAR reference image obtaining unit obtaining a reference image of the satellite including the SAR, the reference image including a ground point of an observation area; a corresponding point extracting unit extracting a corresponding point between the multi-satellite image and the reference image; an image combination and geometric correction performing unit performing image combination and geometrical correction for the multi-satellite image by using the extracted corresponding point; and a HNS detection determining unit determining detection and flowing information of HNS by checking at least one of a pixel luminance value of a SAR satellite image, a pixel temperature value of an infrared satellite image, and a pixel color value of an optical satellite image, the images being included in the corrected multi-satellite image.

In order to accomplish the above object, the present invention provides a continuous detection method of HNS from multiple satellites, the method including: a first step of receiving a multi-satellite image captured by a multi-satellite including a satellite including a SAR, a satellite including an infrared sensor, and a satellite including an electro optical sensor; a second step of obtaining a reference image of the satellite including the SAR which includes a ground reference point of an observation area, and extracting a corresponding point between the reference image and the multi-satellite image; a third step of performing image combination and geometrical correction for the multi-satellite image by using the extracted corresponding point; and a fourth step of determining detection and flowing information of HNS by checking at least one of a pixel luminance value of a SAR satellite image, a pixel temperature value of an infrared satellite image, and a pixel color value of an optical satellite image, the images being included in the corrected multi-satellite image.

Advantageous Effects

As described above, the present invention uses a SAR satellite image obtained from a satellite including a SAR, an infrared satellite image obtained from a satellite including an infrared sensor, and an optical satellite image obtained from a satellite including an electro optical sensor, and thus can continuously and effectively detect HNS leaked into the ocean by complementarily using high resolution images periodically obtained at day time, satellite images with high temporal resolution, satellite images capable of detecting heat changes, and satellite images periodically obtained even though bad weather conditions and regardless of time.

In addition, the present invention extracts HNS detection information extracted from a multi-satellite image by using field observation information directly measured from a buoy in an ocean field where HNS have leaked, and thus can improve the detection accuracy.

MODE FOR INVENTION

Exemplary embodiments of the present invention will be described more fully hereinafter with reference to the accompanying drawings. In the following description of the present invention, detailed descriptions of known functions and components incorporated herein will be omitted when it may make the subject matter of the present invention unclear.

Reference will now be made in detail to various embodiments of the present invention, specific examples of which are illustrated in the accompanying drawings and described below, since the embodiments of the present invention can be variously modified in many different forms. While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims.

It will be understood that when an element is referred to as being "coupled" or "connected" to another element, it can be directly coupled or connected to the other element or intervening elements may be present therebetween. In contrast, it should be understood that when an element is referred to as being "directly coupled" or "directly connected" to another element, there are no intervening elements present. Other expressions that explain the relationship between elements, such as "between" "directly between", "adjacent to", or "directly adjacent to" should be construed in the same way.

Figure 3:
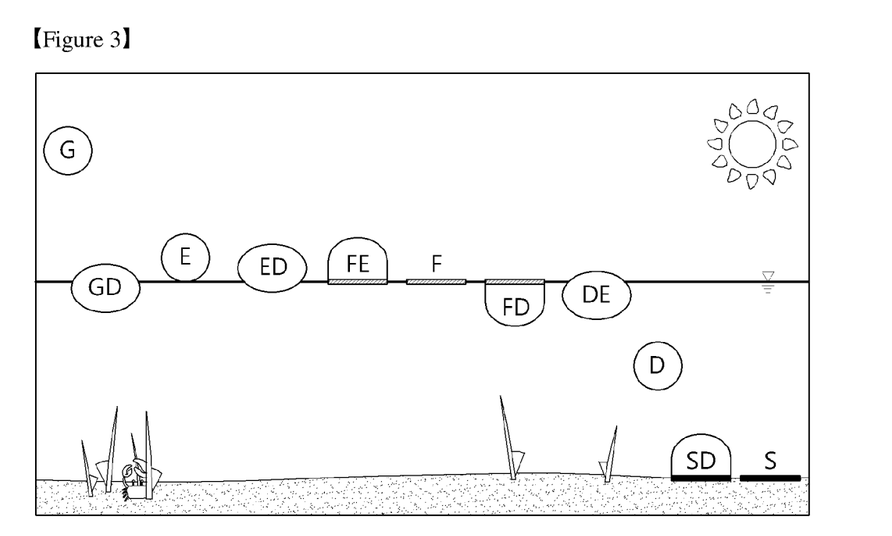
FIG. 3 is a view showing HNS types classified according to diffusion characteristic in the air or seawater.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof According to characteristics of HNS that is diffused into the air or seawater, HNS may be classified into, as shown in FIG. 3, behaviors acting as evaporators, floaters, dissolvers, and sinker. Various types of HNS may be classified in more detail according to: diffusion distribution characteristics into, as shown in FIG. 3, behaviors acting as gas (G), gas/dissolver (GD), evaporator (E), evaporator/dissolver (ED), floater/evaporator (FE), floater (F), floater/dissolver (FD), dissolver/evaporator (DE), dissolver (D), sinker/dissolver (SD), and sinker (S) (Refer to ITOPF (International Tanker Owners Pollution Federation Limited), 2012).

Due the characteristics of artificial satellite images obtained by observing the surface of the sea level, it is practically impossible to detect HNS types spreading and melting quickly into the atmosphere or seawater, such as belonging to behaviors such as acting as an evaporator, dissolver, or sinker.

Meanwhile, HNS belonging to a floater type HNS such as benzene, xylene, styrene, methanol, acetone, etc. may be detected by using satellite images since they are distributed on the sea surface. Particularly, the floater type HNS may cause changes in roughness and reflectance in the sea level, as oils, and thus may be detected by using a conventional oil detection method.

A SAR sensor included in an artificial satellite is an active type high resolution imaging radar that is not affected by weather conditions such as clouds and rain. Particularly, the SAR sensor may perform monitoring for all weather that is not affected by clouds and fog under the bad weather conditions and bad climate conditions, and for day and night.

Figure 4:
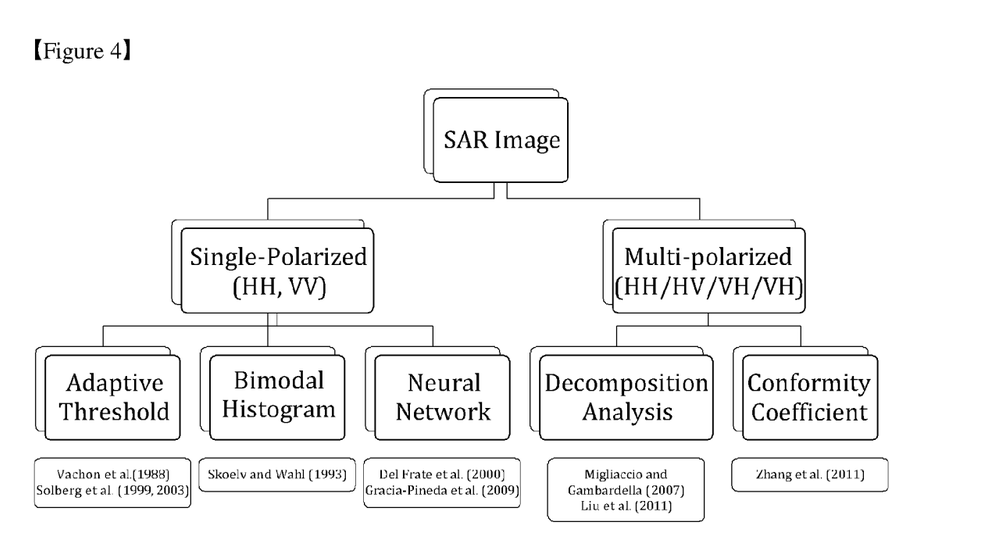
FIG. 4 is a view showing a method of detecting oil leakage using a SAR image.

As described above, as shown in FIG. 4, oil leakage detection methods using SAR images may be classified into: oil leakage detection methods using conventional single polarized images (HH or VV) which are currently widely used; and oil leakage detection methods using multiple polarized images (HH/HV/VH/VV). The method of using multiple polarized images may be useful for HNS detection as well as oil leakage detection because the method uses more additional information according to polarization characteristics.

The present invention may observe a wide spatial range such as a marine environment at a high resolution of several meters or less with an observation width from several tens of km up to 500 km. Particularly, the present invention uses a satellite including a SAR sensor that is capable of monitoring for all weather that is not affected by clouds and fog under the bad weather conditions and bad climate conditions, and for day and night. In addition, the present invention uses a satellite including an electro optical sensor providing excellent resolution. In addition, the present invention uses a satellite including an infrared sensor providing poor resolution, but capable of being used at day and night times, being used under foggy and cloudy conditions and thin cloud as the infrared sensor uses heat radiated from an object, and providing thermal resolution imaging to provide thermal difference analysis between adjacent objects. Observation data obtained from the infrared sensor included in the satellite provides lower resolution than observation data obtained by using visible light. However, wide areal observations in the range of several thousands of km may be performed by using the above data, and thus the data may be used for detecting HNS leakage since detection of thermal changes due to HNS distribution is available.

Hereinafter, a continuously detection method and apparatus of HNS from multiple satellites according to a preferred embodiment of the present invention will be described in detail with reference to the drawings.

Figure 5:
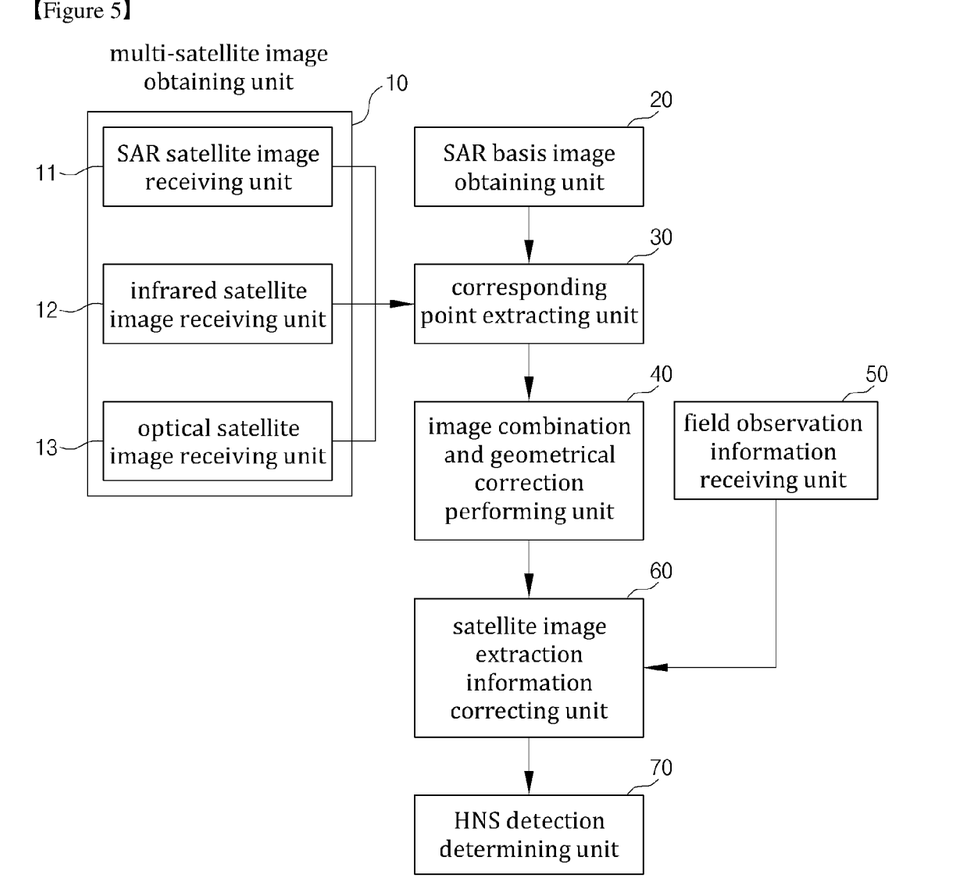
FIG. 5 is a block diagram of a continuous detection apparatus of HNS from multiple satellites according to an embodiment of the present invention.

FIG. 5 is a block diagram showing a continuous detection apparatus of HNS from multiple satellites according to an embodiment of the present invention. As shown in FIG. 5, the continuously detection apparatus of HNS from multiple satellites according to an embodiment of the present invention includes: a multi-satellite image obtaining unit 10; an SAR basis image obtaining unit 20; a corresponding point extracting unit 30; an image combination and geometrical correction performing unit 40; and an HNS detection determining unit 70. In addition, the continuous detection apparatus of HNS from multiple satellites further includes a field observation information receiving unit 50, and a satellite image extraction information correcting unit 60.

The multi-satellite image obtaining unit 10 receives multi-satellite images that are captured from the multi-satellite including a satellite including a SAR, a satellite including an infrared sensor, and a satellite including an electro optical sensor.

The SAR basis image obtaining unit 20 obtains a reference image of the satellite including the SAR, which includes a ground reference point of an observation area.

The corresponding point extracting unit 30 extracts a corresponding point between the multi-satellite image and the reference image, and the image combination and geometrical correction performing unit 40 performs image combination and geometrical correction for the multi-satellite image by using the extracted corresponding point.

The HNS detection determining unit 70 determines detection and flowing information of HNS by checking at least one of a pixel luminance value of an SAR satellite image, a pixel temperature value of an infrared satellite image, and a pixel color value of an optical satellite image which are corrected by the image combination and geometrical correction performing unit 40.

When HNS have leaked into the ocean, the field observation information receiving unit 50 receives ocean field observation information that is measured by using a sensor included in a buoy in the ocean field via wireless communication.

The satellite image extraction information correcting unit 60 corrects HNS detection information extracted from the corrected multi-satellite image by using the ocean field observation information.

Figure 6:
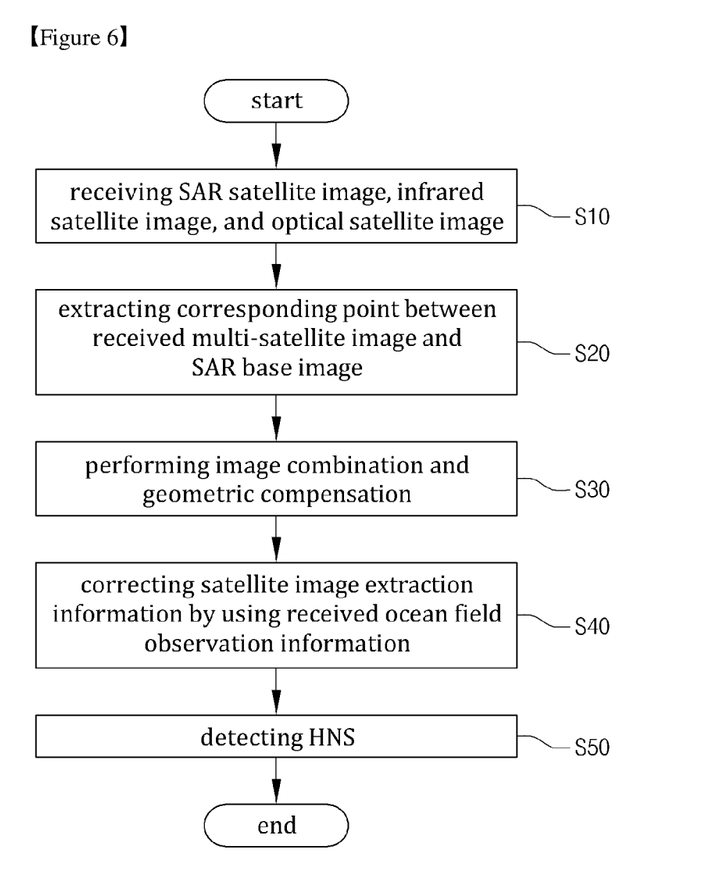
FIG. 6 is a view showing a flowchart of a continuous detection apparatus of HNS from multiple satellites according to another embodiment of the present invention.

FIG. 6 is a view showing a flowchart of a continuous detection method of HNS from multiple satellites according to another embodiment of the present invention. As shown in FIG. 6, the continuous detection method of HNS from multiple satellites according to another embodiment of the present invention includes: a first step S10 of receiving a multi-satellite image captured by a multi-satellite including a satellite including a SAR, a satellite including an infrared sensor, and a satellite including an electro optical sensor; a second step S20 of obtaining a reference image of the satellite including the SAR which includes a ground reference point of an observation area, and extracting a corresponding point between the reference image and the multi-satellite image; a third step S30 of performing image combination and geometrical correction for the multi-satellite image by using the extracted corresponding point; and a fourth step S50 of determining detection and flowing information of HNS by checking at least one of a pixel luminance value of an SAR satellite image, a pixel temperature value of an infrared satellite image, and a pixel color value of an optical satellite image, which are included in the corrected multi-satellite image.

In addition, the continuous detection method of HNS from multiple satellites according to another embodiment of the present invention further includes: a fifth step S40 of receiving, when HNS have leaked into the ocean, ocean field observation information that is measured by using a sensor included in a buoy in the ocean field; and a sixth step S40 of correcting HNS detection information extracted from the corrected multi-satellite image by using the ocean field observation information.

Operation of the continuous detection apparatus of HNS from multiple satellites configured as above according to the embodiment of the present invention will be described in detail.

In the first step S10, a SAR satellite image receiving unit 11 periodically receives SAR satellite images captured by the satellite including the SAR regardless of bad weather conditions and at day and night times. An infrared satellite image receiving unit 12 receives infrared satellite images captured by the satellite including the infrared sensor in quasi-real-time regardless of the sea fog conditions and at both day and night times. In addition, the optical satellite image receiving unit 13 periodically receives at day time optical satellite images captured by the satellite including the electro optical sensor.

In the second step S20, the SAR basis image obtaining unit 20 obtains a based image of the satellite including the SAR which includes a ground reference point of an observation area, and the corresponding point extracting unit 30 extracts a corresponding point between the reference image and the multi-satellite image.

In the third step S30, the image combination and geometrical correction performing unit 40 performs image combination and geometrical correction for the multi-satellite image by using the extracted corresponding point.

In the fourth step S50, the HNS detection determining unit 70 determines detection and flowing information of HNS by checking at least one of a pixel luminance value of the SAR satellite image, a pixel temperature value of the infrared satellite image, and a pixel color value of the optical satellite image which are obtained by correcting the SAR satellite image, the infrared satellite image, and the optical satellite image by the image combination and geometrical correction performing unit 40.

The HNS detection determining unit 70 determines detection and flowing information of the HNS by comparing the pixel luminance value of the SAR satellite image for which image combination and geometrical correction are performed with a preset luminance threshold value. In addition, the HNS detection determining unit 70 determines detection and flowing information of HNS by comparing a seawater temperature value according to a pixel color value of the infrared satellite image for which image combination and geometrical correction are performed with a preset seawater threshold value. In addition, the HNS detection determining unit 70 determines detection and flowing information of HNS by comparing the pixel color value of the optical satellite image for which image combination and geometrical correction are performed with a preset color threshold value.

The luminance threshold value may be variably set according to changes in roughness and reflectance of the sea level caused by HNS belonging to a floater type HNS floating on the seawater surface, the temperature threshold value may be variably set according to changes in temperature of seawater due to HNS distribution, and the color threshold value may be variably set according to changes in reflectance of the sea level due to HNS distribution.

In addition, in step S40, when HNS have leaked into the ocean, the field observation information receiving unit 50 receives ocean field observation information measured by a sensor included in a buoy in the ocean field via wireless communication. The satellite image extraction image correcting unit 60 may correct HNS detection information extracted from the multi-satellite image that is corrected by the image combination and geometrical correction performing unit 40 by using the ocean field observation information.

The ocean field observation information includes observation positional information of the ocean where HNS have leaked, detected material, and distribution degree. The ocean field observation information is information directly measured in the ocean field so that detection accuracy is increased when correction is performed by using the above ocean field observation information. The ocean field observation information is very locally observed information, so that it is difficult to accurately measure the diffusion direction and diffusion range of HNS that have leaked into the ocean. Accordingly, by using multi-satellite images, detection and flowing information (diffusion information) of HNS may be stably and accurately determined by observing the flowing information of seawater, the diffusion direction and diffusion range of HNS.

Although the present invention has been described with reference to the embodiments illustrated in the drawings, those are only examples and may be changed and modified into other equivalent embodiments from the present invention by those skilled in the art. Therefore, the technical protective scope of the present invention should be determined by the scope described in claims.

INDUSTRIAL APPLICABILITY

Applicable to industry of HNS tracking and removal of the same from the ocean

The invention claimed is:
1. A continuous detection apparatus of hazardous and noxious substances (HNS) from multiple satellites, the apparatus comprising:
  a multi-satellite image obtaining unit configured to receive a multi-satellite image captured by the multiple satellites including a satellite including a synthetic aperture radar (SAR), a satellite including an infrared sensor, and a satellite including an electro optical sensor;
  an SAR reference image obtaining unit configured to obtain a reference image of the satellite including the SAR, the reference image including a ground point of an observation area;
  a corresponding point extracting unit configured to extract a corresponding point between the multi-satellite image and the reference image;
  an image combination and geometric correction performing unit configured to perform image combination and geometrical correction for the multi-satellite image by using the extracted corresponding point; and
  an HNS detection determining unit configured to determine detection and flowing information of the HNS by checking at least one of a pixel luminance value of an SAR satellite image, a pixel temperature value of an infrared satellite image, and a pixel color value of an optical satellite image, the optical satellite image being included in the corrected multi-satellite image,
  wherein the HNS detection determining unit is further configured to,
  determine the detection and flowing information of the HNS by comparing the pixel luminance value of the SAR satellite image for which image combination and geometrical correction are performed with a preset luminance threshold value,
  determine the detection and flowing information of the HNS by comparing a seawater temperature according to a pixel color value of the infrared satellite image for which the image combination and the geometrical correction are performed with a preset seawater temperature threshold value, and
  determine detection and flowing information of the HNS by comparing the pixel color value of the optical satellite image for which the image combination and the geometrical correction are performed with a preset color threshold value.

2. The apparatus of claim 1, further comprising:
a field observation information receiving unit configured to receive ocean field observation information measured by a sensor included in a buoy in an ocean field when the HNS have leaked into an ocean, and
a satellite image extraction information correcting unit configured to correct detection information extracted from the corrected multi-satellite image by using the ocean field observation information,
wherein the ocean field observation information includes observation positional information, detected material, and a diffusion degree.

3. The apparatus of claim 1, wherein
the preset luminance threshold value is variably set according to changes in roughness and reflectance of a sea level caused by the HNS belonging to a floater type HNS floating on a seawater surface,
the preset seawater temperature threshold value is variably set according to changes in a seawater temperature caused by HNS distribution, and
the preset color threshold value is variably set according to changes in reflectance of the sea level due to the HNS distribution.

4. The apparatus of claim 1, wherein the multi-satellite image obtaining unit includes:
an SAR satellite image receiving unit configured to receive the SAR satellite image captured by the satellite including the SAR;
an infrared satellite image receiving unit configured to receive the infrared satellite image captured by the satellite including the infrared sensor; and
an optical satellite image receiving unit configured to receive the optical satellite image captured by the satellite including the electro optical sensor.

5. A continuous detection method of hazardous and noxious substances (HNS) from multiple satellites, the method comprising:
receiving a multi-satellite image captured by the multiple satellite including a satellite including a synthetic aperture radar (SAR), a satellite including an infrared sensor, and a satellite including an electro optical sensor;
obtaining a reference image of the satellite including the SAR which includes a ground reference point of an observation area, and extracting a corresponding point between the reference image and the multi-satellite image;
performing image combination and geometrical correction for the multi-satellite image by using the extracted corresponding point; and
determining detection and flowing information of the HNS by checking at least one of a pixel luminance value of an SAR satellite image, a pixel temperature value of an infrared satellite image, and a pixel color value of an optical satellite image, the optical satellite image being included in the corrected multi-satellite image,
wherein the determining further includes,
determining the detection and flowing information of the HNS by comparing the pixel luminance value of the SAR satellite image for which image combination and geometrical correction are performed with a preset luminance threshold value,
determining the detection and flowing information of the HNS by comparing a seawater temperature according to a pixel color value of the infrared satellite image for which image the combination and the geometrical correction are performed with a preset seawater temperature threshold value, and
determining the detection and flowing information of the HNS by comparing the pixel color value of the optical satellite image for which the image combination and the geometrical correction are performed with a preset color threshold value.

6. The method of claim 5, further comprising:
receiving, in response to the HNS having leaked into an ocean, ocean field observation information measured by a sensor included in a buoy in an ocean field; and
correcting HNS detection information extracted from the corrected multi-satellite image by using the ocean field observation information,
wherein the ocean field observation information includes observation positional information, detected material, and a diffusion degree.

7. The method of claim 5, wherein
the preset luminance threshold value is variably set according to change in roughness and reflectance of a sea level caused by the HNS belonging to a floater type HNS floating on a seawater surface,
the preset seawater temperature threshold value is variably set according to changes in a seawater temperature caused by HNS distribution, and
the preset color threshold value is variably set according to changes in reflectance of the sea level due to the HNS distribution.

8. The method of claim 5, wherein the receiving includes:
periodically receiving the SAR satellite image captured by the satellite including the SAR regardless of bad weather conditions and at both day and night times;
receiving the infrared satellite image captured by the satellite including the infrared sensor in quasi-real-time regardless of fog conditions and day and night times; and
periodically receiving at day time the optical satellite image captured by the satellite including the electro optical sensor.

* * * * *